United States Patent
Greven

(10) Patent No.: US 11,766,521 B2
(45) Date of Patent: Sep. 26, 2023

(54) DRIVE SUBASSEMBLY FOR A DRUG DELIVERY DEVICE

(71) Applicant: SANOFI, Paris (FR)

(72) Inventor: Oliver Greven, Frankfurt am Main (DE)

(73) Assignee: Sanofi, Paris (FR)

( * ) Notice: Subject to any disclaimer, the term of this patent is extended or adjusted under 35 U.S.C. 154(b) by 534 days.

(21) Appl. No.: 16/765,311

(22) PCT Filed: Nov. 19, 2018

(86) PCT No.: PCT/EP2018/081784
§ 371 (c)(1),
(2) Date: May 19, 2020

(87) PCT Pub. No.: WO2019/101689
PCT Pub. Date: May 31, 2019

(65) Prior Publication Data
US 2020/0384208 A1 Dec. 10, 2020

(30) Foreign Application Priority Data
Nov. 21, 2017 (EP) ..................................... 17306612

(51) Int. Cl.
*A61M 5/315* (2006.01)
*A61M 5/31* (2006.01)

(52) U.S. Cl.
CPC ...... *A61M 5/31576* (2013.01); *A61M 5/3135* (2013.01); *A61M 5/31501* (2013.01);
(Continued)

(58) Field of Classification Search
CPC ............ A61M 5/31576; A61M 5/3135; A61M 5/31501; A61M 5/31511;
(Continued)

(56) References Cited

U.S. PATENT DOCUMENTS

| 2011/0125100 A1 | 5/2011 | Schwirtz et al. |
| 2017/0080153 A1* | 3/2017 | Maxfield ............. A61M 5/2033 |
| 2017/0246400 A1* | 8/2017 | Stefanov ........... A61M 5/31585 |

FOREIGN PATENT DOCUMENTS

| CN | 102112168 | 6/2011 |
| CN | 103492003 | 1/2014 |

(Continued)

OTHER PUBLICATIONS

PCT International Preliminary Report on Patentability in Application No. PCT/EP2018/081784, dated May 26, 2020, 9 pages.
(Continued)

*Primary Examiner* — Amber R Stiles
*Assistant Examiner* — Nelson Louis Alvarado, Jr.
(74) *Attorney, Agent, or Firm* — Fish & Richardson P.C.

(57) ABSTRACT

The present disclosure relates to a drive subassembly for a drug delivery device, the drive subassembly comprising a proximal housing part comprising a body portion and a closure portion configured as separate parts adapted to be coupled to each other, the closure portion comprising an end face and a guide rod extending from the end face in a distal direction, the guide rod adapted to be inserted into a drive spring; and a plunger, wherein the body portion comprises a profiled slot adapted to engage a plunger boss of the plunger to impede movement of the plunger in the distal direction unless the plunger is rotated to move the plunger boss out of the profiled slot. The disclosure furthermore relates to a proximal housing part for a drug delivery device, to a method for assembling the drive subassembly and to a method for assembling the drug delivery device.

13 Claims, 7 Drawing Sheets

(52) U.S. Cl.
CPC . *A61M 5/31511* (2013.01); *A61M 2005/3142* (2013.01); *A61M 2005/31508* (2013.01); *A61M 2205/8281* (2013.01)

(58) Field of Classification Search
CPC .......... A61M 2005/3142; A61M 2005/31508; A61M 2205/8281; A61M 2005/2006; A61M 2207/00; A61M 5/20
See application file for complete search history.

(56) References Cited

FOREIGN PATENT DOCUMENTS

| | | | |
|---|---|---|---|
| CN | 105517599 | 4/2016 | |
| EP | 2399630 | 12/2011 | |
| JP | 2017-508546 | 3/2017 | |
| WO | WO 2012/105898 | 8/2012 | |
| WO | WO 2012/110579 | 8/2012 | |
| WO | WO 2012/122643 | 9/2012 | |
| WO | WO 2014/166891 | 10/2014 | |
| WO | WO 2015/004052 | 1/2015 | |
| WO | WO 2015/144870 | 10/2015 | |
| WO | WO 2016/169748 | 10/2016 | |
| WO | WO 2016/193375 | 12/2016 | |
| WO | WO 2017/029032 | 2/2017 | |
| WO | WO-2017029032 A1 * | 2/2017 | .......... A61M 5/2033 |

OTHER PUBLICATIONS

PCT International Search Report and Written Opinion in Application No. PCT/EP2018/081784, dated Jan. 21, 2019, 12 pages.

* cited by examiner

DRIVE SUBASSEMBLY FOR A DRUG DELIVERY DEVICE

CROSS REFERENCE TO RELATED APPLICATIONS

The present application is the national stage entry of International Patent Application No. PCT/EP2018/081784, filed on Nov. 19, 2018, and claims priority to Application No. EP 17306612.7, filed on Nov. 21, 2017, the disclosures of which are incorporated herein by reference.

TECHNICAL FIELD

The disclosure generally relates to a proximal housing part for a drug delivery device, to a drive subassembly for a drug delivery device comprising the proximal housing part, to a method for assembling the drive subassembly and to a method for assembling the drug delivery device.

BACKGROUND

Drug delivery devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

Auto-injectors are devices which completely or partially replace activities involved in parenteral drug delivery from standard syringes. These activities may include removal of a protective syringe cap or needle sheath, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

There remains a need for an improved proximal housing part for a drug delivery device, an improved drive subassembly for a drug delivery device comprising the proximal housing part, an improved method for assembling the drive subassembly and an improved method for assembling the drug delivery device.

SUMMARY

An object of the present disclosure is to provide an improved drive subassembly for a drug delivery device, an improved proximal housing part for a drug delivery device, an improved method for assembling the drive subassembly and an improved method for assembling the drug delivery device.

According to the present disclosure, a drive subassembly for a drug delivery device comprises:

a proximal housing part comprising a body portion and a closure portion configured as separate parts adapted to be coupled to each other, the closure portion comprising an end face and a guide rod extending from the end face in a distal direction, the guide rod adapted to be inserted into a drive spring, and a plunger, wherein the body portion comprises a profiled slot adapted to engage a plunger boss of the plunger so as to impede movement of the plunger in the distal direction unless the plunger is rotated so as to move the plunger boss out of the profiled slot.

Separating the closure portion from the body portion allows for manufacturing the closure portion with the guide rod from a more rigid material than the body portion. If the end face is to have a color, only the closure portion has to be colored whereas the body portion can remain uncolored such that shrinkage differences of functional elements on the body portion are avoided.

In an exemplary embodiment, the closure portion is configured to lock in position to the body portion during assembly.

In an exemplary embodiment, the closure portion is configured to lock in position to the body portion in a proximal closure position whereby the end face is at a first distance to the body portion and in a distal closure position whereby the end face is at a second distance to the body portion, the second distance being less than the first distance.

In an exemplary embodiment, the end face abuts the body portion in the distal closure position.

In an exemplary embodiment, the closure portion comprises at least one hook arm extending from the end face in the distal direction, the hook arm having at least one tooth configured to engage a stop in the body portion to lock the closure portion to the body portion.

In an exemplary embodiment, the hook arm has a distal tooth configured to engage a stop in the body portion in the proximal closure position and a proximal tooth configured to engage a stop or the same stop in the body portion in the distal closure position.

In an exemplary embodiment, the body portion comprises at least one clip having an outwardly directed protrusion adapted to engage in a corresponding recess in a distal housing part to lock the proximal housing part to the distal housing part.

In an exemplary embodiment, the closure portion comprises at least one distal support boss adapted to inwardly support the clip when being axially aligned with the clip in the second closure position so as to prevent the clip from inwardly deflecting. Thus, the proximal housing part is locked to the distal housing part and cannot be dismantled such that refilling is prevented or at least impeded. In the first closure position, the distal support boss is axially spaced from the clip so that the clip is free to deflect inwardly, e.g. during assembly of the proximal housing portion into the distal housing part.

According to an aspect of the present disclosure, a drive subassembly for a drug delivery device comprises the proximal housing part as described above and a plunger, wherein the body portion comprises a profiled slot adapted to engage a plunger boss of the plunger so as to impede movement of the plunger in the distal direction unless the plunger is rotated so as to move the plunger boss out of the profiled slot.

In an exemplary embodiment, the closure portion comprises at least one proximal support boss adapted to engage a plunger boss when being axially aligned with said plunger boss such that the plunger is prevented from rotating and the plunger boss cannot move out of the profiled slot, when the closure portion is in the proximal closure position. Thus, inadvertent release of the plunger prior to assembly of the drive subassembly to a control subassembly may be prevented.

In an exemplary embodiment, the drive subassembly further comprises a plunger release mechanism, comprising:
- a first plunger boss on the plunger,
- a second plunger boss on the plunger,
- the profiled slot,
- a sleeve rib on a sleeve adapted to interact with the second plunger boss, wherein the profiled slot comprises a first angled surface adapted to engage the first plunger boss to induce a torque in a first rotational direction to the plunger, a wall for limiting movement of the first plunger boss in the first rotational direction when engaged to the first angled surface, the profiled slot furthermore comprising a second angled surface adapted to engage the first plunger boss to induce a torque in a second rotational direction to the plunger, the second rotational direction being opposite to the first rotational direction.

In an exemplary embodiment, the sleeve rib comprises a distal face, a longitudinal face and an angled face.

In an exemplary embodiment, the drive subassembly further comprises a closure rib arranged on the closure portion, the closure rib being configured to engage one of the plunger bosses so as to induce a torque to the plunger in the second rotational direction when the first plunger boss is engaged to the first angled surface and when the closure portion is moved into the second closure position. During final assembly of a drug delivery device, the closure portion may be moved from the first closure position to the second closure position to initiate or prime the plunger release mechanism. As opposed to a priming step, in which the sleeve would be moved to initiate the plunger release mechanism, the presently disclosed solution does not require access to the sleeve from the distal direction so that a distal surface of a cap covering the distal end of the drug delivery device may be closed.

The drive subassembly may be part of a drug delivery device, further comprising a control subassembly comprising a distal housing part adapted to retain a syringe.

In an exemplary embodiment, the drug delivery device further comprises a syringe containing a medicament.

According to an aspect of the present disclosure, a proximal housing part for a drug delivery device comprises a body portion and a closure portion configured as separate parts adapted to be coupled to each other, the closure portion comprising an end face and a guide rod extending from the end face in a distal direction, the guide rod adapted to be inserted into a drive spring.

According to an aspect of the present disclosure, a method for assembling a drive subassembly of a drug delivery device comprises:
- providing a proximal housing part as described above with the body portion separate from the closure portion,
- placing the body portion on a rod of an assembly jig,
- arranging a drive spring onto the rod and into the body portion,
- arranging a plunger onto the drive spring and moving the plunger toward the body portion to compress the drive spring,
- locking the plunger to the body portion,
- removing the rod out of the drive spring,
- inserting the guide rod of the closure portion into the drive spring and moving the closure portion into a closure position relative to the body portion.

In an exemplary embodiment, the plunger is locked to the body portion by rotation.

In an exemplary embodiment, the closure portion is moved into a proximal closure position after the plunger has been locked to the body portion by rotation, wherein in the proximal closure position, a proximal support boss on the closure portion engages a plunger boss such that the plunger is prevented from rotating to unlock the plunger from the body portion.

According to an aspect of the present disclosure, a method for assembling a drug delivery device comprises the above described method for assembling the drive subassembly, wherein after assembly of the drive subassembly, the proximal housing part is inserted into a distal housing part, whereby one or more clips on the body portion having respective outwardly directed protrusions enter the distal housing part until the one or more protrusions become axially aligned with one or more recesses in the distal housing part allowing the clips to relax outward such that the protrusions engage in the one or more recesses.

In an exemplary embodiment, after engagement of the one or more protrusions in the one or more recesses, the closure portion is moved into a distal closure position, whereby one or more distal support bosses on the closure portion become axially aligned with the one or more clips so that the clips cannot deflect inwards.

In an exemplary embodiment, in the distal closure position, the proximal support boss is axially misaligned with the plunger boss such that the plunger is no longer prevented from rotating.

In an exemplary embodiment, when the closure portion is moved into the distal closure position, a closure rib arranged on the closure portion engages a plunger boss so as to induce a torque to the plunger.

In an exemplary embodiment, the plunger, the drive spring and the guide rod are arranged along a center axis of the drive subassembly.

In an exemplary embodiment, the profiled slot is coaxial with but offset from the center axis.

In an exemplary embodiment, the drive spring is arranged within the plunger. In other embodiments, the drive spring may be arranged around the plunger.

In an exemplary embodiment, the plunger boss extends radially from the plunger.

In an exemplary embodiment, the plunger is releasably locked.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1A:
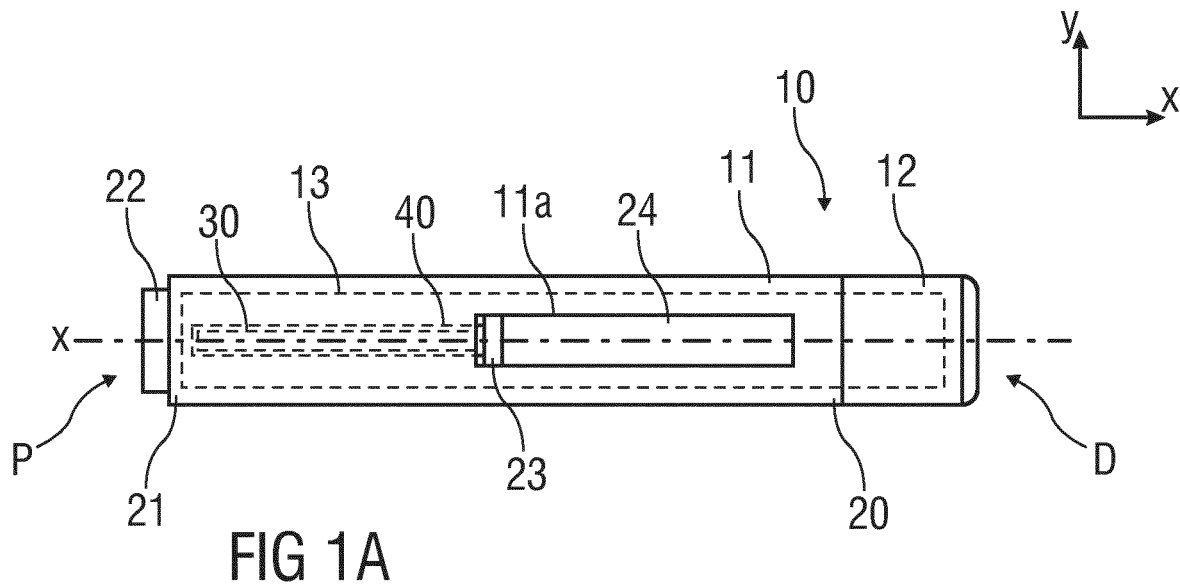
FIG. 1 is a schematic view of an exemplary embodiment of a drug delivery device.
Figure 1B:
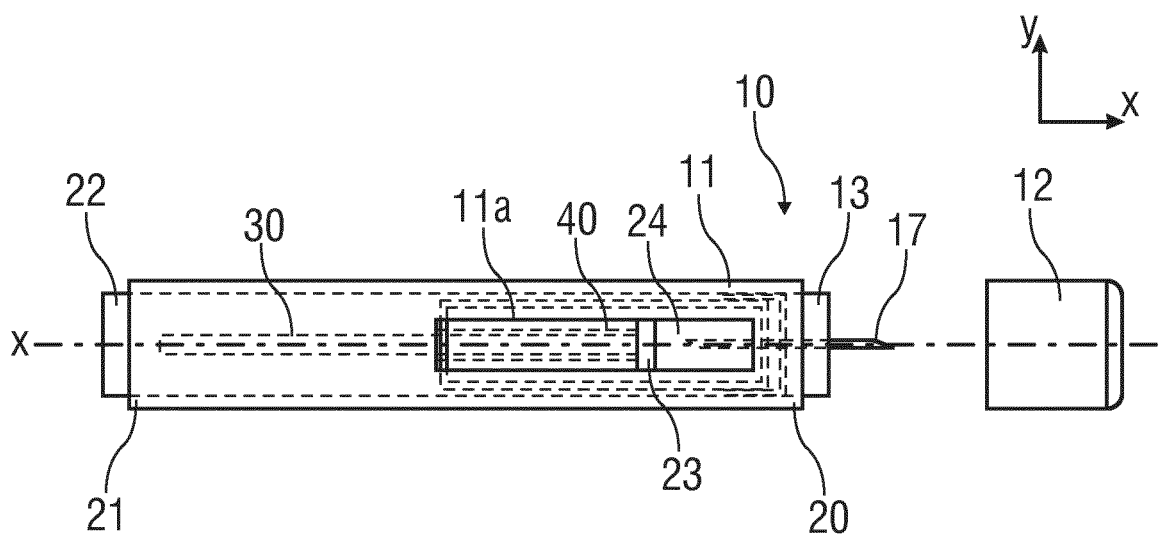

According to some embodiments of the present disclosure, an exemplary drug delivery device 10 is shown in FIGS. 1A and 1B.

Device 10, as described above, is configured to inject a drug or medicament into a patient's body.

Device 10 includes a housing 11 which typically contains a reservoir containing the medicament to be injected (e.g., a syringe 24 or a container) and the components required to facilitate one or more steps of the delivery process.

Device 10 can also include a cap assembly 12 that can be detachably mounted to the housing 11, in particular on a distal or front end D of the device 10. Typically, a user must remove cap assembly or cap 12 from housing 11 before device 10 can be operated. Removal of the cap 12 may at the same time remove a protective needle sheath from the needle 17. The cap 12 may be engaged to the protective needle sheath by friction or by a barb or the like.

As shown, housing 11 is substantially cylindrical and has a substantially constant diameter along the longitudinal axis X. The housing 11 has a distal housing part 20 and a proximal housing part 21. The term "distal" refers to a location that is relatively closer to a site of injection, and the term "proximal" refers to a location that is relatively further away from the injection site.

Device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from distal housing part 20 of housing 11. Insertion of the needle 17 can occur via several mechanisms. For example, the needle 17 may be fixedly located relative to housing 11 and initially be located within an extended needle sleeve 13. Proximal movement of the sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to housing 11. Such insertion can be triggered by movement of sleeve 13 or by another form of activation, such as, for example, a button 22. As shown in FIGS. 1A and 1B, button 22 is located at a proximal or back end P of the housing 11. However, in other embodiments, button 22 could be located on a side of housing 11. In further embodiments, the button 22 has been deleted and is replaced for instance by a sleeve trigger mechanism, e.g. provided by pushing the needle sleeve 13 inside the housing when the drug delivery device is put onto an injection side.

Other manual or automated features can include drug injection or needle retraction, or both. Injection is the process by which a bung or piston 23 is moved from a proximal location within a container or syringe 24 to a more distal location within the syringe 24 in order to force a medicament from the syringe 24 through needle 17.

In some embodiments, an energy source, e.g. a drive spring 30 is arranged in a plunger 40 and is under compression before device 10 is activated. A proximal end of the drive spring 30 can be fixed within proximal housing part 21 of housing 11, and a distal end of the drive spring 30 can be configured to apply a compressive force to a proximal surface of piston 23. Following activation, at least part of the energy stored in the drive spring 30 can be applied to the proximal surface of piston 23. This compressive force can act on piston 23 to move it in a distal direction. Such distal movement acts to compress the liquid medicament within the syringe 24, forcing it out of needle 17.

Following injection, the needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of the sleeve 13 has moved past a distal end of the needle 17, and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal housing part 20. A compressed retraction spring, when activated, can supply sufficient force to the syringe 24 to move it in a proximal direction. Following sufficient retraction, any relative movement between the needle 17 and the housing 11 can be locked with a locking mechanism. In addition, button 22 or other components of device 10 can be locked as required.

In some embodiments, the housing may comprise a window 11a through which the syringe 24 can be monitored.

The drug delivery device 10 may be divided in two subassemblies, a control subassembly and a drive subassembly 10.1. This allows for improving flexibility as to the time and location of manufacture of the subassemblies and final assembly with the syringe 24.

Figure 2:
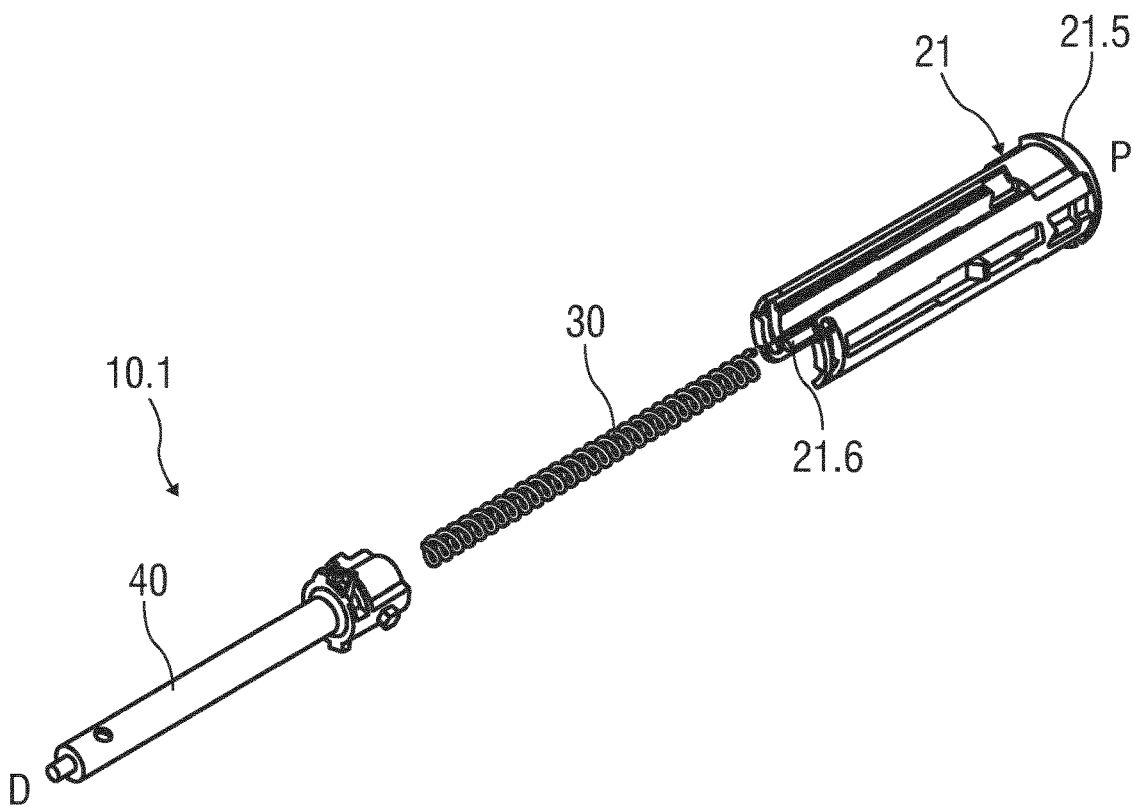
FIG. 2 is a schematic perspective exploded view of a drive subassembly of a drug delivery device.

FIG. 2 is a perspective exploded view of the drive subassembly 10.1. The drive subassembly 10.1 comprises components used to displace the medicament from the syringe 24. If the viscosity or volume of the medicament M in the syringe 24 is varied, only parts of the drive subassembly 10.1 may need to be changed. The drive subassembly 10.1 comprises the plunger 40, the drive spring 30 and the proximal housing part 21 of the housing 11. In an exemplary embodiment, the drive subassembly 10.1 may be assembled in a process which requires virtually only axial motion except for the plunger 40. In order to assemble the drive subassembly 10.1 the drive spring 30 is inserted into the plunger 40 and the plunger 40 is inserted in the proximal housing part 21 in the proximal direction P thereby compressing the drive spring 30. Once the plunger 40 reaches a compressed position it is rotated by an angle, e.g. approximately 30° to lock it to the proximal housing part 21. In an exemplary embodiment the proximal housing part 21 could have a cam surface which could induce this rotation prior to the plunger 40 reaching the compressed position.

In another exemplary embodiment, the plunger 40 may be locked to the proximal housing part 21 in a different way without being rotated, e.g. by a snap or latch on one of the plunger 40 or proximal housing part 21 engaging a stop on the other of the plunger 40 and the proximal housing part 21.

Furthermore, a feedback element, e.g. a spring element may be provided to indicate an event, e.g. an end of dose, by providing an audible and/or tactile feedback.

In an exemplary embodiment, the proximal housing part 21 may comprise a proximal end face 21.5 and a guide rod 21.6 extending from the end face 21.5 in the distal direction D, the guide rod 21.6 adapted to be inserted into the drive spring 30, e.g. to guide it as it expands during an injection.

Figure 3:
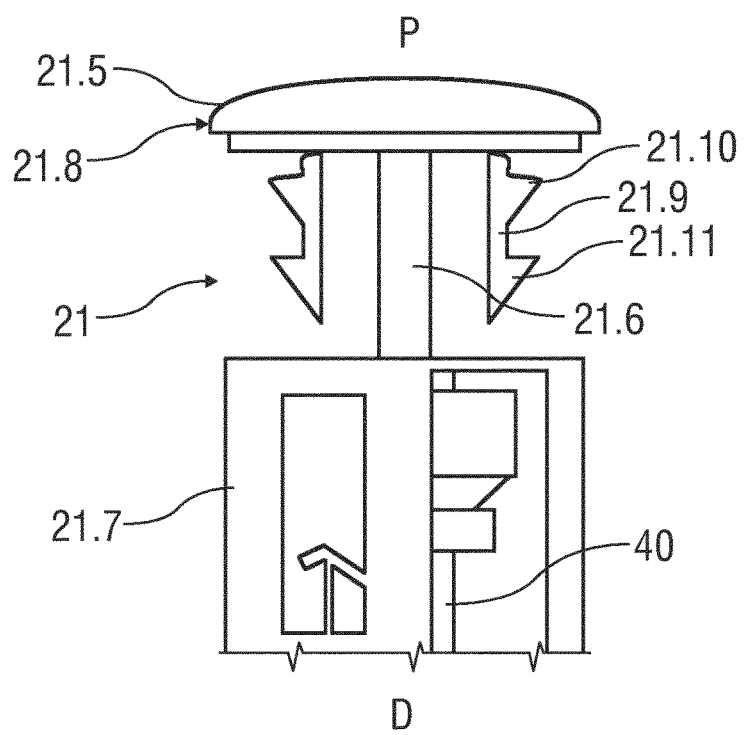
FIG. 3 is a schematic view of an exemplary embodiment of a proximal housing part of a housing.

FIG. 3 is a schematic view of an exemplary embodiment of the proximal housing part 21.

In an exemplary embodiment, the proximal housing part 21 may comprise a body portion 21.7 and a closure portion 21.8 configured as distinct parts adapted to be coupled to each other. The closure portion 21.8 comprises the end face 21.5 and the guide rod 21.6 which may be integrally formed, whereas the body portion 21.7 may comprise casework and functional components, e.g. for coupling the drive subassembly 10.1 to the control subassembly, for locking the plunger 40 relative to the proximal housing part 21, etc. The components of the body portion 21.7 may be integrally formed. Separating the closure portion 21.8 from the body portion 21.7 allows for manufacturing the closure portion 21.8 with the guide rod 21.6 from a more rigid material than the body portion 21.7. In an exemplary embodiment, the end face 21.5 may be colored. In this case, only the closure portion 21.8 may be colored.

In an exemplary embodiment, the closure portion 21.8 is configured to lock in position to the body portion 21.7 during assembly in a proximal closure position P1 whereby the end face 21.5 is at a first distance to the body portion 21.7 and in a distal closure position P2 whereby the end face 21.5 is at a second distance to the body portion 21.7, the second distance being less than the first distance. In an exemplary embodiment, the end face 21.5 may abut the body portion 21.7 in the distal closure position P2. In an exemplary embodiment, the closure portion 21.8 comprises at least one hook arm 21.9 extending from the end face 21.5 in the distal direction D, e.g. in parallel with the guide rod 21.6, the hook arm 21.9 having a distal tooth 21.10 configured to engage a stop (not shown) in the body portion 21.7 in the proximal closure position P1 and a proximal tooth 21.11 configured to engage a stop (not shown) or the same stop in the body portion 21.7 in the distal closure position P2.

In another exemplary embodiment, the closure portion 21.8 may be configured to lock in position to the body portion 21.7 during assembly in only one closure position and the hook arm 21.9 may only have one tooth.

Figure 4:
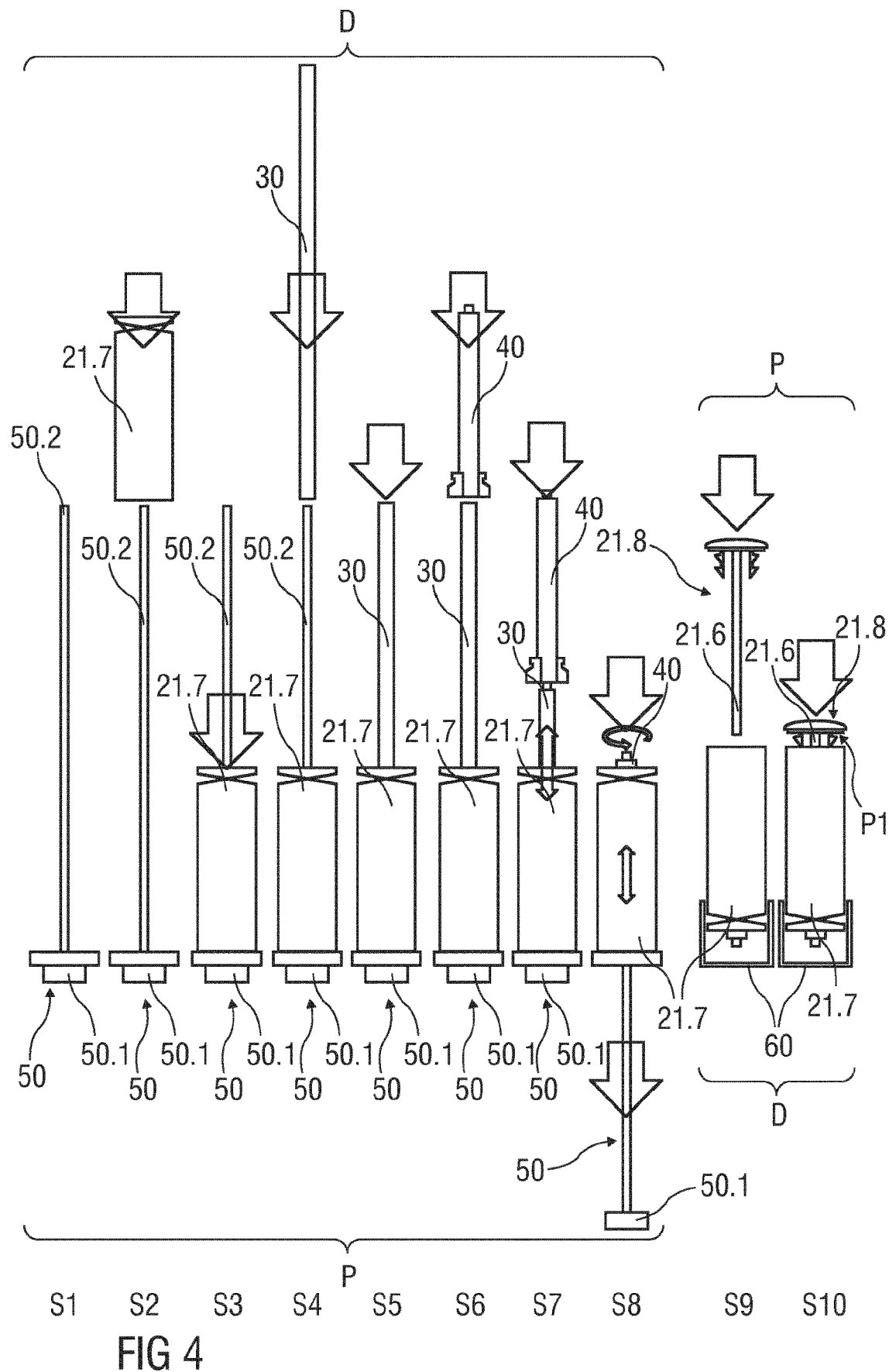
FIG. 4 is a schematic view of a drive subassembly in different states during assembly.

FIG. 4 is a schematic view of the drive subassembly 10.1 in different states during assembly.

In a state S1 an assembly jig 50 is provided, the assembly jig 50 having a base 50.1 and a rod 50.2 extending from the base 50.1 and configured to be inserted into the drive spring 30.

In a state S2, the body portion 21.7 is being placed with a proximal end ahead on the rod 50.2 or the rod 50.2 is inserted into the proximal end of the body portion 21.7. A feedback component may have been mounted to the body portion 21.7 prior to step S2.

In a state S3, the rod 50.2 is located within the body portion 21.7 which rests on the base 50.1.

In a state S4, the drive spring 30 is being arranged onto the rod 50.2 towards the body portion 21.7 or the rod 50.2 is inserted into the drive spring 30. A feedback component may have been mounted to the body portion 21.7 prior to step S4.

In a state S5, the drive spring 30 has been inserted into the body portion 21.7 while being arranged onto the rod 50.2.

In a state S6, the plunger 40 is arranged onto the drive spring 30 towards the body portion 21.7 or the drive spring 30 is inserted into the plunger 40.

In an exemplary embodiment, the plunger 40 could be arranged onto the drive spring 30 before the drive spring is arranged onto the rod 50.2.

In a state S7, the plunger 40 is moved further toward the body portion 21.7 thereby compressing the drive spring 30 which is prevented from buckling as it is guided by the rod 50.2.

In a state S8, the plunger 40 has been moved into the body portion 21.7 into a locking position where the plunger 40 may be locked to the body portion 21.7, e.g. by rotation. In another exemplary embodiment, the plunger 40 may be locked to the body portion 21.7 in a different way without being rotated, e.g. by a snap or latch on one of the plunger 40 or body portion 21.7 engaging a stop on the other of the plunger 40 and the body portion 21.7.

The assembly jig 50 may now be pulled out of the drive spring 30 in the proximal direction P as the drive spring 30 is at least almost completely located within the plunger 40 so it cannot buckle.

In a state S9, the guide rod 21.6 of the closure portion 21.8 is inserted into the proximal end of the body portion 21.7 and into the drive spring 30. The body portion 21.7 may have been turned upside down for this step and placed with a distal end ahead into a mounting aid 60.

In a state S10, the guide rod 21.6 of the closure portion 21.8 has been inserted into the proximal end of the body portion 21.7 and into the drive spring 30 and the closure portion 21.8 has arrived in the proximal closure position P1, in which the closure portion 21.8 locks in position to the body portion 21.7. In another exemplary embodiment, the closure portion 21.8 may have only one closure position in which it arrives in state S10.

Figure 5:
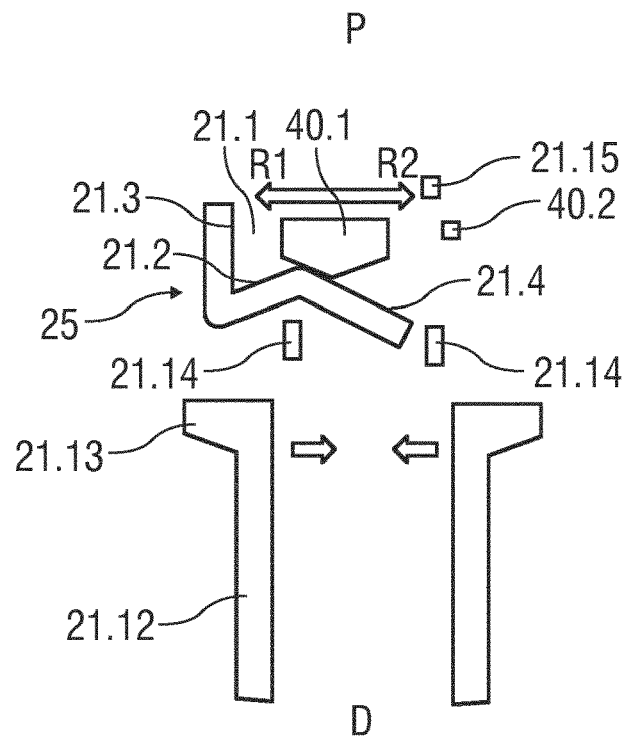
FIG. 5 is a schematic view of internals of the proximal housing part comprising a plunger release mechanism.

FIG. 5 is a schematic view of the internals of the proximal housing part 21 comprising a plunger release mechanism 25. The plunger release mechanism 25 controls the activation of syringe emptying. The plunger release mechanism 25 is adapted to release the plunger 40 once the sleeve 13 is depressed and reaches a retracted position within the housing 11.

The plunger release mechanism 25 comprises a first plunger boss 40.1 arranged on the plunger 40 and a profiled slot 21.1 in the proximal housing part 21 of the housing 11. The profiled slot 21.1 comprises a first angled surface 21.2 adapted to engage the first plunger boss 40.1 to induce a torque in a first rotational direction R1 to the plunger 40, a wall 21.3 for limiting movement of the first plunger boss 40.1 in the first rotational direction R1 when engaged to the first angled surface 21.2. Furthermore, the profiled slot 21.1 comprises a second angled surface 21.4 adapted to engage the first plunger boss 40.1 to induce a torque in a second rotational direction R2 to the plunger 40. The plunger 40 may comprise further plunger bosses or ribs adapted to interact with corresponding features on the sleeve 13 so that the plunger 40 rotates once the sleeve 13 is depressed and reaches a retracted position within the housing 11 in such a way that the first plunger boss 40.1 moves in the second rotational direction R2 out of the profiled slot 21. The plunger release mechanism 25 may be configured as shown in FIGS. 6, 7, 8 and 19 or FIGS. 23A-E of WO 2015/004052 A1 which is herewith incorporated by reference in its entirety. Likewise, the plunger release mechanism 25 may be configured as shown below in FIGS. 10 to 12.

The proximal housing part 21, in particular the body portion 21.7 thereof, further comprises one or more clips 21.12 having outwardly directed protrusions 21.13 adapted to engage in corresponding recesses in the distal housing part 20 of the housing 11. The protrusions 21.13 may be ramped so as to be inwardly deflected when engaging a proximal end of the distal housing part 20 allowing them to be inserted into the distal housing part 20. The closure portion 21.8 may comprise one or more distal support bosses 21.14 and one or more proximal support bosses 21.15, the distal support bosses 21.14 adapted to inwardly support the clips 21.12 when being axially aligned with them so as to prevent them from inwardly deflecting. The proximal support boss 21.15 is adapted to engage a plunger boss, e.g. the first plunger boss 40.1 or a second plunger boss 40.2 when being axially aligned with said plunger boss such that the plunger 40 is prevented from rotating in the second rotational direction R2.

In the state shown in FIG. 5, the closure portion 21.8 is spaced from the body portion 21.7 as shown in FIG. 3 and has not yet arrived in the proximal closure position P1. Referring again to FIG. 5, the distal support bosses 21.14 are thus located proximally from the clips 21.12 so that the clips 21.12 are free to deflect inwards. The proximal boss 21.15 is located proximally from the second plunger boss 40.2 so that the plunger 40 is free to rotate. Starting from this state, the plunger 40 is rotated in the first rotational direction R1 such that the first plunger boss 40.1 engages the first angled surface 21.2. The plunger 40, under force from the drive spring 30 in the distal direction D, therefore tends to further rotate in the first rotational direction R1 but is prevented from doing so by the first plunger boss 40.1 abutting the wall 21.3.

Figure 6:
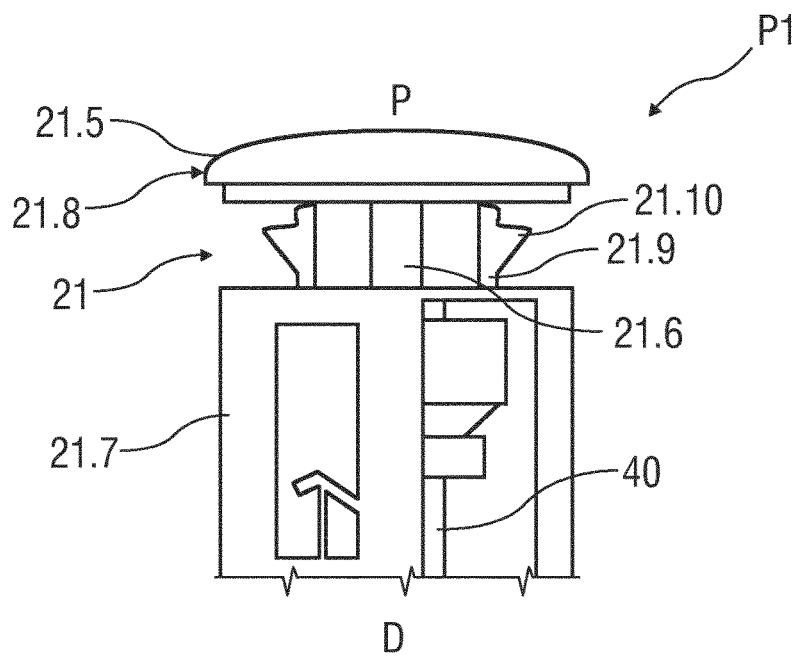
FIG. 6 is a schematic view of the proximal housing part with a closure portion moved into a body portion and having arrived at a proximal closure position.
Figure 7:
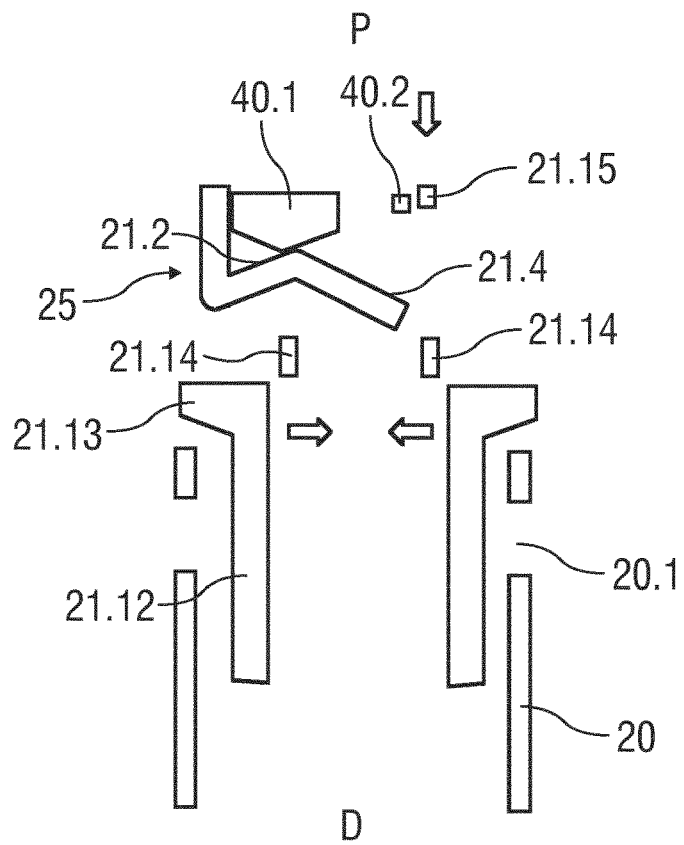
FIG. 7 is a schematic detail view of the internals of the proximal housing part.

FIG. 6 is a schematic view of the proximal housing part 21 with the closure portion 21.8 moved in the distal direction D into body portion 21.7 and having arrived at the proximal closure position P1. FIG. 7 is a respective schematic detail view of the internals of the proximal housing part 21. Due to the movement of the closure portion 21.8 into the proximal closure position P1, the proximal support boss 21.15 has been axially aligned with the second plunger boss 40.2 such that the plunger 40 is prevented from rotating in the second rotational direction R2 and can thus not inadvertently be released. The distal support bosses 21.14 are still axially misaligned with the clips 21.12 so that they are free to deflect inwards.

In this state, the proximal housing part 21 may be assembled to the distal housing part 20. During such assembly, the proximal housing part 21 is inserted into the distal housing part 20, whereby the clips 21.12 enter the distal housing part 20. The protrusions 21.13 may abut the distal housing part 20 and, due to their ramps, be inwardly deflected upon further movement in the distal direction D toward the distal housing part 20 until the protrusions 21.13 become axially aligned with recesses 20.1 in the distal housing part 20 allowing the clips 21.12 to relax outward such that the protrusions 21.13 engage in these recesses 20.1.

Figure 8:
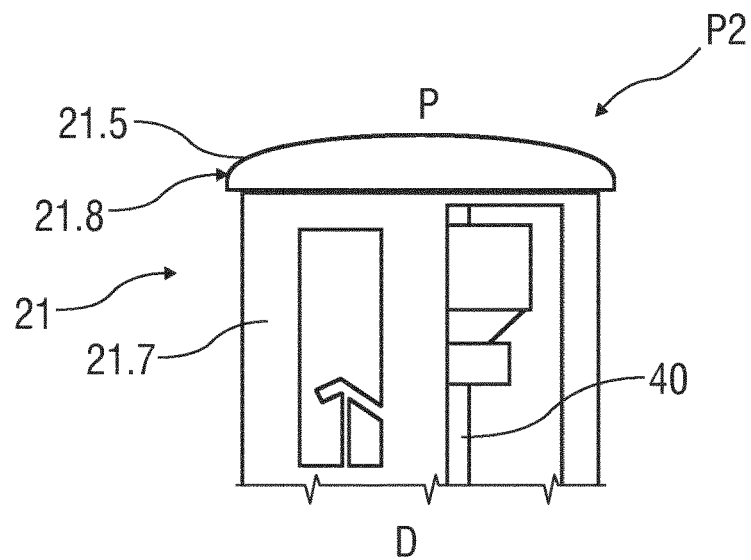
FIG. 8 is a schematic view of the proximal housing part with the closure portion having arrived at a distal closure position.
Figure 9:
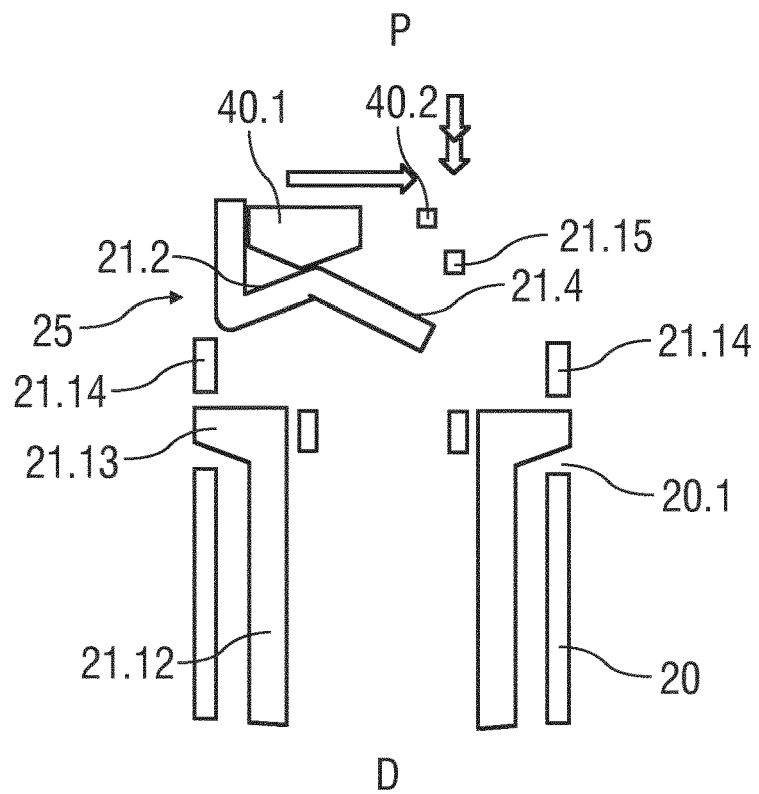
FIG. 9 is a respective schematic detail view of the internals of the proximal housing part.

FIG. 8 is a schematic view of the proximal housing part 21 with the closure portion 21.8 moved further in the distal direction D into body portion 21.7 and having arrived at the distal closure position P2. FIG. 9 is a respective schematic detail view of the internals of the proximal housing part 21. Due to the movement of the closure portion 21.8 into the distal closure position P2, the proximal support boss 21.15 has been axially misaligned with the second plunger boss 40.2 such that the plunger 40 is no longer prevented from rotating in the second rotational direction R2 by the proximal support boss 21.15. However, as the first plunger boss 40.1 engages the first angled surface 21.2, the plunger 40, under force from the drive spring 30 in the distal direction D, still tends to further rotate in the first rotational direction R1 and will not yet rotate in the second rotational direction R2. Likewise, due to the movement of the closure portion 21.8 into the distal closure position P2, the distal support bosses 21.14 are axially aligned with the clips 21.12 so that they cannot deflect inwards. Thus, the proximal housing part 21 is locked to the distal housing part 20 and cannot be dismantled such that refilling is prevented or at least impeded.

Figure 10:
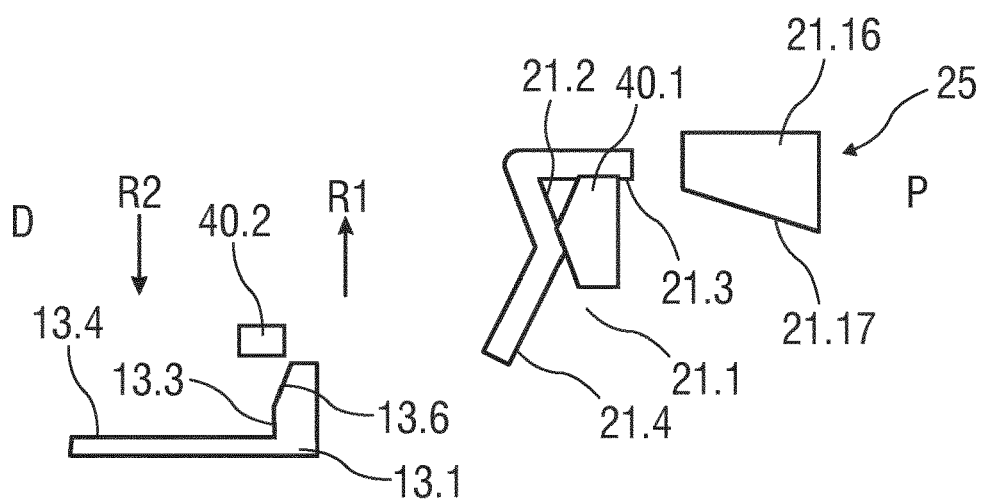
FIG. 10 is a schematic view of an exemplary embodiment of a plunger release mechanism.

FIG. 10 is a schematic view of an exemplary embodiment of a plunger release mechanism 25.

The plunger release mechanism 25 comprises the plunger 40, the proximal housing part 21, and the sleeve 13 interacting with each other. The sleeve 13 and the proximal housing part 21 are configured to move only in parallel with the longitudinal axis X relative to each other whereas the plunger 40 can move both in parallel with the longitudinal axis X and rotate about the longitudinal axis X. The parts of the plunger release mechanism 25 may be essentially rigid and require no deformation in order to function correctly.

The parts arranged for engaging the plunger 40, proximal housing part 21 and sleeve 13 comprise:
a first plunger boss 40.1 on the plunger 40,
a second plunger boss 40.2 on the plunger 40,
a profiled slot 21.1 in the proximal housing part 21, e.g. in the body portion 21.7 adapted to interact with the first plunger boss 40.1,
a sleeve rib 13.1 on the sleeve 13 comprising a distal face 13.3, a longitudinal face 13.4 and an angled face 13.6 adapted to interact with the second plunger boss 40.2, wherein one end of the distal face 13.3 is adjacent the longitudinal face 13.4 and another, opposite end of the distal face 13.3 is adjacent the angled face 13.6, The profiled slot 21.1 comprises a first angled surface 21.2 adapted to engage the first plunger boss 40.1 to induce a torque in a first rotational direction R1 to the plunger 40, a wall 21.3 for limiting movement of the first plunger boss 40.1 in the first rotational direction R1 when engaged to the first angled surface 21.2. Furthermore, the profiled slot 21.1 comprises a second angled surface 21.4 adapted to engage the first plunger boss 40.1 to induce a torque in a second rotational direction R2 to the plunger 40, the second rotational direction R2 being opposite to the first rotational direction R1.

The first angled surface 21.2 and/or the second angled surface 21.4 may have an angle in a range from 30° to 70° relative to a perpendicular on the longitudinal axis X of the drug delivery device 10 which may also be the longitudinal axis of the plunger 40.

A closure rib 21.16 is arranged on the closure portion 21.8, the closure rib 21.16 having an angled face 21.17 adapted to engage the first plunger boss 40.1 or any other plunger boss so as to induce a torque to the plunger 40 when the first plunger boss 40.1 is engaged to the first angled surface 21.2 and when the closure portion 21.8 is moved into a closure position, e.g. the second closure position P2. In FIG. 10, the closure portion 21.8 is in the first closure position P1 so that the closure rib 21.16 is located proximally from the first plunger boss 40.1 and does not engage it.

During assembly of the drive subassembly 10.1 the plunger 40 with the drive spring 30 is inserted into the proximal housing part 21, e.g. as shown in FIG. 4. Once the plunger 40 reaches a proximal position the first plunger boss 40.1 is axially aligned with the profiled slot 21.1. By rotating the plunger 40 in the first rotational direction R1 by an angle, e.g. approximately 30°, the first plunger boss 40.1 is moved into the profiled slot 21.1. In this position the first angled surface 21.2 moves the first plunger boss 40.1 against the wall 21.3 by inducing a torque to the plunger 40 in the first rotational direction R1 due to the drive spring 30 biasing the plunger 40 in the distal direction D.

In order to assemble the drug delivery device 10, a syringe 24 may be inserted into the control subassembly which may comprise the distal housing part 20 of the housing 11.

Afterwards, the drive subassembly 10.1 is inserted into the control subassembly in the distal direction D so that the sleeve rib 13.1 arrives in proximity to the second plunger boss 40.2, wherein the second plunger boss 40.2 is rotationally spaced from the sleeve rib 13.1 to allow it being moved in the proximal direction P during assembly such that the second plunger boss 40.2 does not engage any part of the sleeve rib 13.1 in this state. The proximal housing part 21 and the distal housing part 20 may comprise snap connections to lock them together when assembled. During the final assembly of the drug delivery device 10, the closure portion 21.8 may be moved from the first closure position P1 to the second closure position P2 to initiate or prime the plunger release mechanism 25. As opposed to a priming step, in which the sleeve 13 would be moved to initiate the plunger release mechanism 25, the presently disclosed solution does not require access to the sleeve 13 from the distal direction D so that a distal surface of the cap 12 may be closed.

Figure 11:
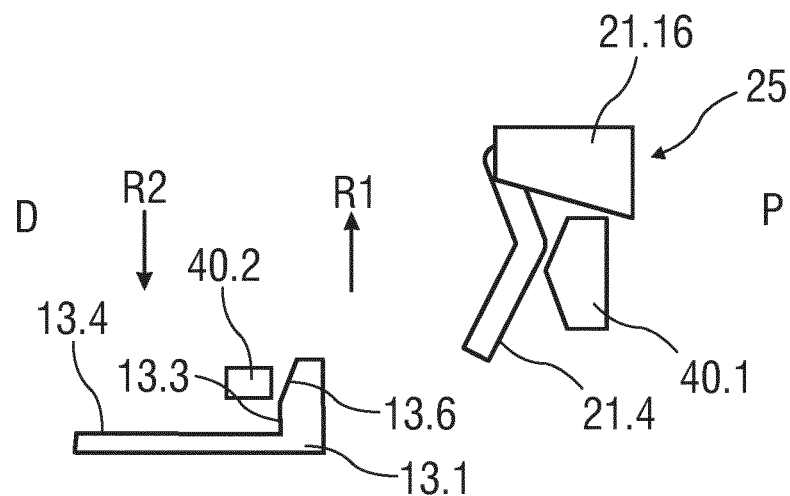
FIG. 11 is a schematic view of the plunger release mechanism during final assembly.
Figure 12:
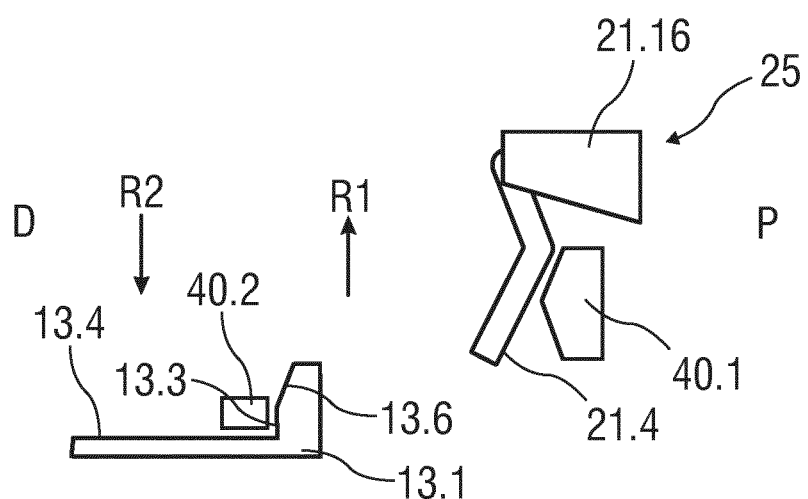
FIG. 12 is a schematic view of the plunger release mechanism during final assembly.

FIG. 11 shows the plunger release mechanism 25 during the final assembly. The closure portion 21.8 is moved in the distal direction D into the second closure position P2 such that the closure rib 21.16 engages the first plunger boss 40.1 and induces a torque on the plunger 40 in the second rotational direction R2. Due to the induced torque, the first plunger boss 40.1 moves in the first rotational direction R1 and engages the second angled surface 21.4. Due to the first plunger boss 40.1 engaging the second angled surface 21.4 and the drive spring 30 acting on the plunger 40 in the distal direction D, the plunger 40 rotates further in the second rotational direction R2. At the same time, the second plunger boss 40.2 is moved in the second rotational direction R2 where it engages the sleeve rib 13.1, first the angled face 13.6 moving the sleeve 13 slightly in the proximal direction P during further rotation of the plunger 40 as shown in FIG. 11, and then the distal face 13.3 until the second plunger boss 40.2 also abuts the longitudinal face 13.4 so that rotation of the plunger 40 is halted as shown in FIG. 12. The abutment of the second plunger boss 40.2 on the distal face 13.3 limits movement of the sleeve 13 in the distal direction D, e.g. under the action of a sleeve spring (not illustrated). The slight movement of the sleeve 13 in the proximal direction P during engagement of the second plunger boss 40.2 to the angled face 13.6 ensures that the sleeve 13 does not push the cap 12 in the distal direction D so that the cap 12 does not inadvertently pull a protective needle sheath off the needle 17. The load of the drive spring 30 is resolved within the proximal housing part 21 by the first plunger boss 40.1 engaging the profiled slot 21.1.

In an exemplary embodiment, the sleeve rib 13.1 may not have the angled face 13.6 but only the distal face 13.3 and the longitudinal face 13.4.

A sequence of operation of the drug delivery device 10 may be as follows:

The user removes the cap assembly 12 pulling it in the distal direction D away from the housing 11. Removal of the cap assembly 12 may at the same time remove the protective needle sheath from the needle 17.

The sleeve 13 is in an extended position protruding from the housing 11 in the distal direction D. The extended position may be defined by the second plunger boss 40.2 proximally abutting the distal face 13.3 of the sleeve rib 13.1.

The user may then press the drug delivery device 10 with the sleeve 13 ahead against an injection site, e.g. a patient's skin thereby moving the sleeve 13 from the extended position towards a retracted position against the bias of the shroud spring.

As the sleeve 13 is being moved from the extended position towards the retracted position the second plunger boss 40.2 moves (starting from the position shown in FIG. 12) relative to the sleeve 13 in the distal direction D guided along the longitudinal face 13.4 of the sleeve rib 13.1.

In an exemplary embodiment the longitudinal face 13.4 of the sleeve rib 13.1 may comprise an interruption or bump feature (not illustrated) for creating an increase in the force required to depress the sleeve 13 further. This may be used to indicate to the user that needle insertion would commence with further depression of the sleeve 13. Up until this point, the user is free to remove the drug delivery device 10 from the injection site and reposition as the sleeve 13 will re-extend to its initial position under the force of the shroud spring.

If the user continues pressing the drug delivery device 10 against the injection site the sleeve 13 is moved into the retracted position exposing the needle 17 and inserting it into the injection site.

Once the sleeve 13 is depressed into the retracted position, and the needle 17 inserted, the second plunger boss 40.2 will have moved distally beyond the sleeve rib 13.1 such that the plunger 40 is no longer prevented from rotating in the second rotational direction R2 due to the torque induced by the drive spring 30 and the first plunger boss 40.1 engaging the second angled surface 21.4 on the profiled slot 21.1. The plunger 40 rotates in the second rotational direction R2 due to this torque and the first plunger boss 40.1 comes clear of the profiled slot 21.1. The plunger 40 is thus released and advances the piston 23 in the distal direction D displacing the medicament from the syringe 24 through the needle 17. The release of the first or second plunger boss 40.1, 40.2 may provide audible feedback that delivery of the medicament has started.

The skilled person readily understands that, wherever two components are engaged by ramps or angled faces to rotate one of the components by translating the other or vice versa, either one of these two engaged components or both of them may have a ramp or angled face to engage the respective other component.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days).

In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding housing part.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining housing part" or "CDR" refer to short polypeptide sequences within the variable housing part of both heavy and light chain polypeptides that are primarily responsible for mediating specific antigen recognition. The term "framework housing part" refers to amino acid sequences within the variable housing part of both heavy and light chain polypeptides that are not CDR sequences, and are primarily responsible for maintaining correct positioning of the CDR sequences to permit antigen binding. Although the framework housing parts themselves typically do not directly participate in antigen binding, as is known in the art, certain residues within the framework housing parts of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 10 drug delivery device
10.1 drive subassembly
11 housing
11a window
12 cap assembly
13 sleeve
13.1 sleeve rib
13.3 distal face
13.4 longitudinal face
13.6 angled face
17 needle
20 distal housing part
20.1 recess
21 proximal housing part
21.1 profiled slot
21.2 first angled surface
21.3 wall
21.4 second angled surface
21.5 proximal end face
21.6 guide rod
21.7 body portion
21.8 closure portion
21.9 hook arm
21.10 distal tooth
21.11 proximal tooth
21.12 clip
21.13 protrusion
21.14 distal support boss
21.15 proximal support boss
21.16 closure rib
21.17 angled face
22 button
23 piston
24 syringe
25 plunger release mechanism
30 drive spring
40 plunger
40.1 first plunger boss
40.2 second plunger boss
50 assembly jig
50.1 base
50.2 rod
60 mounting aid
D distal end, distal direction
P proximal end, proximal direction
P1 proximal closure position
P2 distal closure position
R1 first rotational direction
R2 second rotational direction
X longitudinal axis

The invention claimed is:

1. A drug delivery device, comprising:
a drive subassembly, comprising:
a proximal housing part comprising a body portion and a closure portion configured as separate parts adapted to be coupled to each other, the closure portion comprising an end face and a guide rod extending from the end face in a distal direction, the guide rod adapted to be inserted into a drive spring, and
a plunger,
wherein the body portion comprises a profiled slot adapted to engage a plunger boss of the plunger so as to impede movement of the plunger in the distal direction unless the plunger is rotated so as to move the plunger boss out of the profiled slot, and wherein the end face is a proximal end of the drug delivery device; and
a control subassembly comprising a distal housing part adapted to retain a syringe.

2. The drug delivery device of claim 1, further comprising the syringe retained within the distal housing part of the control subassembly.

3. The drug delivery device of claim 2, wherein the syringe contains a medicament.

4. The drug delivery device of claim 1, wherein the closure portion is configured to lock in position to the body portion in a proximal closure position whereby the end face is at a first distance to the body portion and in a distal closure position whereby the end face is at a second distance to the body portion, the second distance being less than the first distance.

5. The drug delivery device of claim 4, wherein the closure portion comprises at least one hook arm extending from the end face in the distal direction, the at least one hook arm having at least one tooth configured to engage a stop in the body portion to lock the closure portion to the body portion.

6. The drug delivery device of claim 4, wherein the body portion comprises at least one clip having an outwardly directed protrusion adapted to engage in a corresponding recess in a distal housing part to lock the proximal housing part to the distal housing part.

7. The drug delivery device of claim 6, wherein the closure portion comprises at least one distal support boss adapted to inwardly support the at least one clip when being axially aligned with the at least one clip in the distal closure position so as to prevent the at least one clip from inwardly deflecting.

8. The drug delivery device of claim 1, wherein the closure portion comprises at least one proximal support boss adapted to engage a plunger boss when being axially aligned with the plunger boss such that the plunger is prevented from rotating and the plunger boss cannot move out of the profiled slot, when the closure portion is in the proximal closure position.

9. The drug delivery device of claim 1, wherein the drive subassembly further comprises a plunger release mechanism, the plunger release mechanism comprising:

a first plunger boss on the plunger;
a second plunger boss on the plunger;
the profiled slot; and
a sleeve rib on a sleeve adapted to interact with the second plunger boss.

10. The drug delivery device of claim 9, wherein the profiled slot comprises:
a first angled surface adapted to engage the first plunger boss to induce a torque in a first rotational direction to the plunger; and
a wall for limiting movement of the first plunger boss in the first rotational direction when engaged to the first angled surface.

11. The drug delivery device of claim 10, wherein the profiled slot further comprises a second angled surface adapted to engage the first plunger boss to induce a torque in a second rotational direction to the plunger, the second rotational direction being opposite to the first rotational direction.

12. The drug delivery device of claim 11, wherein the sleeve rib comprises a distal face, a longitudinal face, and an angled face.

13. The drug delivery device of claim 11, wherein the drive subassembly further comprises a closure rib arranged on the closure portion, the closure rib being configured to engage one of the plunger bosses so as to induce a torque to the plunger in the second rotational direction when the first plunger boss is engaged to the first angled surface and when the closure portion is moved into the second closure position.

* * * * *

UNITED STATES PATENT AND TRADEMARK OFFICE
CERTIFICATE OF CORRECTION

| | |
|---|---|
| PATENT NO. | : 11,766,521 B2 |
| APPLICATION NO. | : 16/765311 |
| DATED | : September 26, 2023 |
| INVENTOR(S) | : Greven |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 552 days.

Signed and Sealed this
Twelfth Day of November, 2024

Katherine Kelly Vidal
*Director of the United States Patent and Trademark Office*